United States Patent
Johs et al.

(10) Patent No.: US 7,450,231 B2
(45) Date of Patent: *Nov. 11, 2008

(54) DEVIATION ANGLE SELF COMPENSATING SUBSTANTIALLY ACHROMATIC RETARDER

(75) Inventors: Blaine D. Johs, Lincoln, NE (US); Steven E. Green, Lincoln, NE (US); Craig M. Herzinger, Lincoln, NE (US); Duane E. Meyer, Lincoln, NE (US)

(73) Assignee: J.A. Woollam Co., Inc., Lincoln, NE (US)

(*) Notice: Subject to any disclaimer, the term of this patent is extended or adjusted under 35 U.S.C. 154(b) by 120 days.

This patent is subject to a terminal disclaimer.

(21) Appl. No.: 11/633,138

(22) Filed: Dec. 4, 2006

(65) Prior Publication Data

US 2008/0100842 A1 May 1, 2008

Related U.S. Application Data

(63) Continuation-in-part of application No. 11/590,408, filed on Oct. 31, 2006.

(60) Provisional application No. 60/733,910, filed on Nov. 4, 2005.

(51) Int. Cl.
G01J 4/00 (2006.01)
G02B 5/30 (2006.01)

(52) U.S. Cl. ............... 356/365; 356/368; 359/496; 359/497; 359/494

(58) Field of Classification Search ......... 356/364–369, 356/356; 359/494, 496, 497
See application file for complete search history.

(56) References Cited

U.S. PATENT DOCUMENTS

| | | | | |
|---|---|---|---|---|
| 4,822,150 A * | 4/1989 | Duarte | .......... | 359/487 |
| 5,706,212 A | 1/1998 | Thompson et al. | ......... | 364/525 |
| 5,751,482 A * | 5/1998 | Challener, IV | ......... | 359/487 |
| 5,963,325 A | 10/1999 | Johs et al. | ......... | 306/364 |
| 6,084,674 A | 7/2000 | Johs et al. | ......... | 356/364 |
| 6,084,675 A | 7/2000 | Herzinger et al. | ......... | 356/369 |
| 6,100,981 A | 8/2000 | Johs et al. | ......... | 356/364 |
| 6,118,537 A | 9/2000 | Johs et al. | ......... | 356/369 |
| 6,141,102 A | 10/2000 | Johs et al. | ......... | 356/364 |
| 6,353,477 B1 | 3/2002 | Johs et al. | ......... | 356/369 |
| 2002/0181101 A1 * | 12/2002 | Appel | ......... | 359/487 |
| 2006/0023308 A1 * | 2/2006 | Hunt | ......... | 359/500 |

* cited by examiner

*Primary Examiner*—L. G Lauchman
(74) *Attorney, Agent, or Firm*—James D. Welch

(57) ABSTRACT

A substantially achromatic multiple element compensator system for use in wide spectral range (for example, 190-1700 nm) rotating compensator spectroscopic ellipsometer and/or polarimeter systems. Multiple total internal reflections enter retardance into an entered beam of electromagnetic radiation, and the elements are oriented to minimize changes in the net retardance vs. the input beam angle resulting from changes in the position and/or rotation of the system of elements.

18 Claims, 8 Drawing Sheets

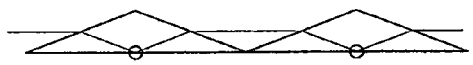
FIG. 9a
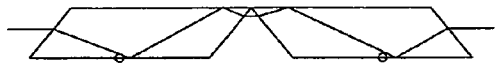
FIG. 10a
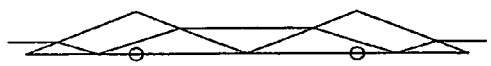
FIG. 9b
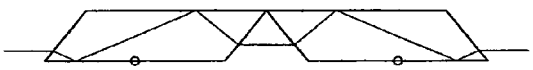
FIG. 10b
Beam angle=+1°, Ψ=56.953°, Δ=70.425°
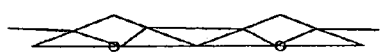
FIG. 11a
Beam angle=0°, Ψ=56.940°, Δ=70.419°
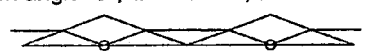
FIG. 11b
Beam angle=-1°, Ψ=56.953°, Δ=70.425°
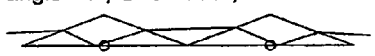
FIG. 11c
Beam angle=+1°, Ψ=52.357°, Δ=114.232°
FIG. 11d
Beam angle=0°, Ψ=52.349°, Δ=114.221°
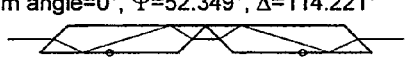
FIG. 11e
Beam angle=-1°, Ψ=52.357°, Δ=114.232°
FIG. 11f
FIG. 11
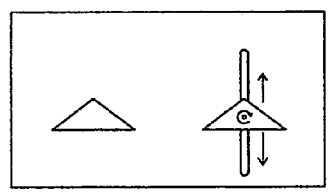
FIG. 12a
FIG. 12b

DEVIATION ANGLE SELF COMPENSATING SUBSTANTIALLY ACHROMATIC RETARDER This application is a CIP of Co-Pending application Ser. No. 11/590,408 Filed Oct. 31, 2006, and Claims Benefit of Provisional Application Ser. No. 60/733,910 Filed Sep. 4, 2005.

TECHNICAL FIELD

The present invention relates to retarders for entering retardance between orthogonal components of a beam of polarized electromagnetic radiation, and more particularly is a multiple sequential element, substantially achromatic retarder which uses multiple total internal reflections of a single, undeviated, transmitted beam to generate retardance. Said reflections are oriented to minimize changes in the net retardance vs. the input beam angle over a wide spectral range, (for example, 190-1700 nm), as a function of system translation and rotation. The retarders are suitable for use in a rotating compensator ellipsometer or polarimeter.

BACKGROUND

To obtain acceptable ellipsometer and/or polarimeter performance over a wide spectral range, compensator-based ellipsometer and/or polarimeter designs require a compensator element that provides retardance within a certain acceptable range over the entire spectral range. Traditionally, birefringent waveplates of quartz or $MgF_2$ have been used as compensator elements in rotating element designs. A single waveplate exhibits a (1/wavelength) dependence in retardance vs. wavelength, while a dual/multiple waveplate design, (as disclosed in U.S. Pat. No. 6,353,477), can minimize the effect of the (1/wavelength) dependence.

With the present invention in mind, known relevant Patents are:
U.S. Pat. No. 5,706,212 to Thompson et al.;
U.S. Pat. No. 6,353,477 to Johs et al.;
U.S. Pat. No. 5,963,325 to Johs et al.;
U.S. Pat. No. 6,141,102 to Johs et al.;
U.S. Pat. No. 6,084,675 to Herzinger et al.
U.S. Pat. No. 6,118,537 to Johs et al.;
U.S. Pat. No. 6,100,981 to Johs et al.;
U.S. Pat. No. 6,084,674 to Johs et al.

Need remains for additional compensator system which provide improved characteristics.

DISCLOSURE OF THE INVENTION

First, it is noted that the present invention can be applied in an ellipsometer or polarimeter system comprising:
a) a source of electromagnetic radiation;
b) a polarizer;
c) a stage for supporting a sample;
d) an analyzer; and
e) a detector;
said ellipsometer or polarimeter system further comprising at least one rotatable compensator system present at least one location selected from the group consisting of:
between said source of electromagnetic radiation and said stage for supporting a sample; and
between said stage for supporting a sample and said detector;
said at least one rotatable compensator comprising at least two sequential elements oriented with respect to one another such that an entered electromagnetic beam undergoes total internal reflection at least once in each of the elements, with the sequence, orientation, geometry, and symmetry of the elements being such that the locus of the output beam is substantially undeviated from that of the input beam by a translation of the system, and the locus of the output beam angle is substantially undeviated from that of the input beam by a rotation of the system.

The present invention is a system for introducing a relative phase retardation between orthogonal components of a polarized electromagnetic beam. Said system consists of at least two sequential elements, and said beam undergoes total internal reflection at least once in each of said elements. Importantly, the sequence, orientation, geometry, and symmetry of the elements in the system is such that the locus of an exiting output beam is substantially undeviated from that of the input beam by a translation of the system, and the exiting output beam angle is substantially undeviated from that of the input beam by a rotation of the system.

One embodiment provides that two triangular shaped prisms comprise the elements. Preferred, non-limiting, design provides that the angles of said triangular prisms are 26, 128, and 26, and fabrication of the prisms can be, but is not necessarily, from fused silica.

Another embodiment provides that two parallelogram shaped rhombs are used for the elements. Preferred, non-limiting, design provides that angles of the parallelogram shaped rhombs are 36, 144, 36, and 144 degrees or 45, 135, 45 and 135 degrees, and again, fabrication of the parallelogram can be, but is not necessarily, from fused silica.

Another embodiment provides that four right angle prisms are used for elements. Preferred, non-limiting, design provides that angles are 45, 90 and 45, and again, fabrication of the prism can be, but is not necessarily, from fused silica.

Further, at least one of the elements can comprise a mechanism for translating and/or tilting at least one of the elements with respect to another element, for the purpose of aligning the elements of the system so as to reduce deviation between the locus of an output beam as compared to that of a beam input to said system.

The present invention can be better described as being a system for introducing a relative phase retardation into orthogonally polarized components of an electromagnetic beam entered thereinto, said system consisting of at least two sequential elements oriented with respect to one another such that said entered electromagnetic beam undergoes total internal reflection at least once in each of the at least two elements;
the sequence, orientation, geometry, and symmetry of the elements being such that the output beam position is substantially undeviated by a translation of the system, and the output beam angle is substantially undeviated by a rotation of the system.

The elements can be similar triangular shaped prisms each having:
first and second sides of equal length which project from one another at an angle greater than ninety degrees therebetween, and
a third side oriented opposite said greater than ninety degree angle,
said at least two similar triangular shaped prisms being oriented with respect to one another such that the third sides thereof are substantially colinear;

such that a beam of electromagnetic radiation caused to enter the first side of one thereof, at a non-normal angle thereto, is refracted so that it internally reflects from said third side thereof, then exits said second side thereof in a direction such that it then enters the first side of another thereof at a non-normal angle thereto, is refracted so that it internally reflects from said third side thereof, then exits said second side thereof. The angles of the triangular prism can be 26, 128, and 26 degrees and the prisms can be fabricated from of fused silica.

The elements can be parallelogram shaped rhombs, each said rhomb having first, second, third and forth sides, said first and third sides being parallel to one another and said second and forth sides being parallel to one another, said first and second, and said third and forth sides meeting one another at angles greater than ninety degrees therebetween, and said second and third sides and said first and forth sides meeting one another at angles less than ninety degrees therebetween, said at least two parallelogram shaped rhombs being oriented with their second sides being substantially colinear and with their forth sides thereof being substantially colinear;

such that a beam of electromagnetic radiation caused to enter the first side of one thereof, at a non-normal angle thereto, is refracted so that it internally reflects from said second and forth side thereof, then exits said third side thereof in a direction such that it then enters the first side of another thereof at a non-normal angle thereto, is refracted so that it internally reflects from said second and forth side thereof, then exits said third side thereof. The angles of the parallelogram shaped rhomb can be 36, 144, 36, and 144 degrees or 45, 135, 45 and 135 degrees, and can be fabricated from of fused silica.

The elements can be rhombs, each said rhomb having first, second, third and forth sides, said first and third sides being parallel to one another and said second and forth sides being parallel to one another, said first and second, and said third and forth sides meeting one another at angles greater than ninety degrees therebetween, and said second and third sides and said first and forth sides meeting one another at angles less than ninety degrees therebetween, said at least two Parallelogram shaped rhombs being oriented with their first and third sides being substantially parallel to one another;

such that a beam of electromagnetic radiation caused to enter the first side of one thereof, at substantially a normal angle thereto, then proceeds so that it internally reflects from said second and forth side thereof, then exits said third side thereof in a direction such that it then enters the first side of another thereof at a substantial normal angle thereto, then proceeds so that it internally reflects from said second and forth side thereof, then exits said third side thereof;

said system being characterized in that at least one of the first and third sides of at least one of the parallelogram shaped rhombs has a coating thereupon which has a different, (eg. lower), refractive index than does the material from which said corresponding parallelogram shaped rhomb is comprised. The angles of the parallelogram shaped rhomb can be 36, 144, 36, and 144 degrees or 45, 135, 45 and 135 degrees, and the rhombs can be fabricated from of fused silica, with the coating being $MgF_2$.

The elements can be at least four sequential elements, said beam undergoing total internal reflection once in each of the elements, said system being characterized in that each of said at least four elements are right angle prisms having right angle sides adjacent to the right angle thereof and a side opposite the right angle thereof; said right angle prisms being oriented with respect to one another such that, as viewed in side elevation, the first right angle prism is positioned so that its side opposite the right angle thereof is facing downward and to the right, and so that directly above the first right angle prism is present the second right angle prism, which is oriented so that its side opposite the right angle thereof is facing upward and to the left, and so that directly to the right of the second right angle prism is the third right angle prism, which is oriented so that its side opposite the right angle thereof is facing upward and to the right, and so that directly below the third right angle prism is positioned the forth right angle prism, oriented so that its side opposite the right angle thereof is facing downward and to the left. The angles of the right angle prisms can be 45, 90 and 45 degrees and the right angle prisms can be fabricated from of fused silica.

As recited above, any of the foregoing embodiments can be further characterized by at least one selection from:

at least one of the sequential elements has a mechanism for translating and/or tilting the element, for the purpose of aligning the system such that the output beam is substantially undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge can be rotated with respect to another wedge and/or both wedges can be rotated simultaneously, for the purpose of aligning the system such that the output beam is substantially undeviated from said input beam;

A present invention method involves providing a compensator system comprising at least two elements oriented with respect to one another such that an entered electromagnetic beam undergoes total internal reflection at least once in each of the elements, with the sequence, orientation, geometry, and symmetry of the elements being such that the locus of output beam from said system is substantially undeviated from that of the input beam by a translation of the system, and the locus of the output beam angle is substantially undeviated from that of the input beam by a rotation of the system;

said method comprising the steps of:
  a) providing a system for introducing a relative phase retardation into orthogonally polarized components of an electromagnetic beam, said system comprising of at least two sequential elements, said beam undergoing total internal reflection at least once in each of the elements;
  b) causing a beam of electromagnetic radiation to enter said system via a first of said at least two sequential elements and pass through said at least two sequential elements while undergoing at least one total internal reflection in each;

such that the exiting beam has retardation entered thereinto via said internal reflections, and such that the locus of the exiting beam is substantially undeviated from that of the entering beam.

A coating can be provided on at least one surface of at least one of element, said coating having a refractive index less than or greater than that of the material from which said element is comprised.

Said method can further comprise providing an additional sequential multiple wedge system in said system, wherein one said wedge can be rotated with respect to another thereof and/or both wedges can be rotated simultaneously, for the purpose of aligning the system such that the output beam from said forth right angle prism is substantially undeviated from the beam input to said first right angle prism.

The present invention will be better understood by reference to the Detailed Description Section of this Specification, in combination with reference to the Drawings.

BRIEF DESCRIPTION OF THE DRAWINGS

FIGS. 9a, 9b, 10a and 10b show that the most useful property of the new retarder design is that as the angle of the input beam is changed, the resulting transmitted bean angle does not change.

FIGS. 11a-11f show very small beam polarization change, in terms of PSI and DELTA, for a given change in beam angle.

FIG. 12a demonstrates translation and rotation capability for an element of a two sequential element retarder system.

FIG. 12b shows a two wedge system which allows for relative rotation therebetween.

DETAILED DISCLOSURE OF THE INVENTION

Figure 1:
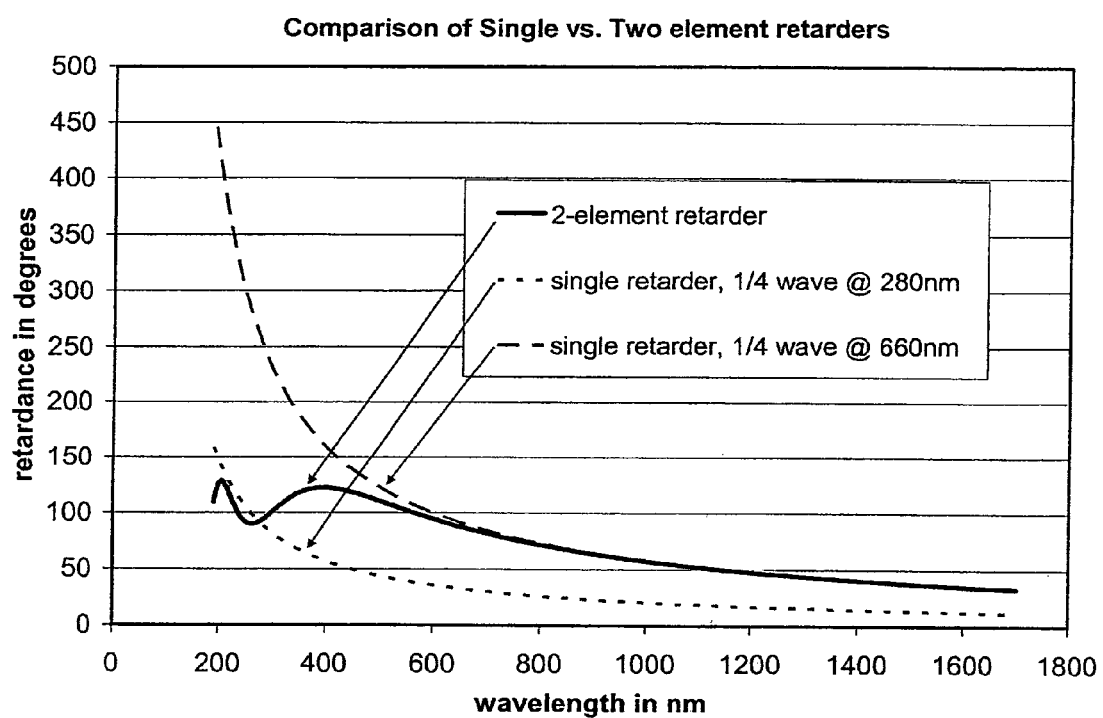
FIG. 1 shows retardance results from a retarder comprising two birefringent waveplates over a spectroscopic range.
Figure 2:
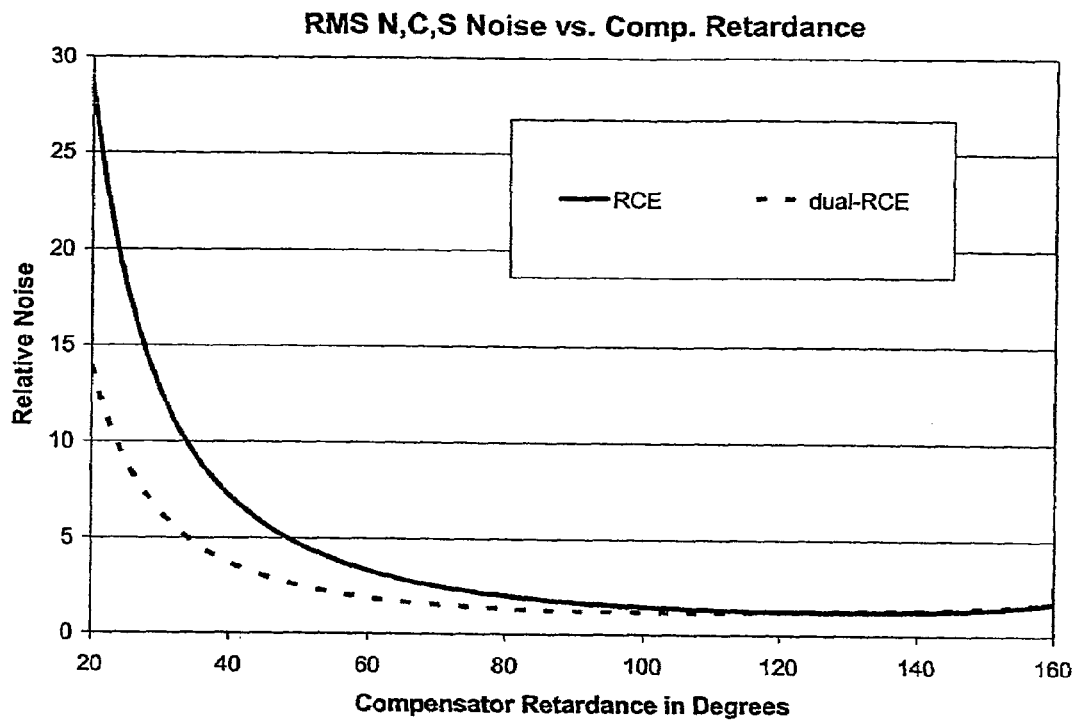
FIG. 2 shows the Root Mean Squared (RMS) noise in ellipsometric parameters N, C and S.

Turning now to FIG. 1, as introduction, results from a retarder comprising two birefringent waveplates are shown. Note that the retardance varies from 35-130 degrees over the typical UV-VIS-NIR spectral range of 190-1700 nm. FIG. 2 shows the Root Mean Squared (RMS) noise in the ellipsometric parameters;

$N = \cos(2\psi)$;

$C = \sin(2\psi)\cos(\Delta)$; and $S = \sin(2\psi)\sin(\Delta)$;

for the rotating compensator ellipsometer (RCE) and dual rotating compensator ellipsometer (dual-RCE) configurations as a function of compensator retardance. See FIG. 13 for insight to the construction of a rotating compensator ellipsometer (RCE) with one or two of the shown Compensators (C), (C') (C") considered as present. Continuing, for said rotating compensator ellipsometer (RCE) configuration it is disclosed that it has been determined to be beneficial to keep the retardance between 80 and 160 degrees, as this keeps the relative RMS N,C,S noise to less than 2.0. In that regard the dual-RCE configuration is slightly more forgiving over the retardance range is 60-160 degrees. It should be appreciated that FIGS. 1 and 2 show that using birefringent waveplates through which a beam of electromagnetic radiation is caused to pass, in wide spectral range rotating compensator ellipsometer systems, compromises the noise performance of the system.

In view of the above disclosure, it is disclosed that an alternative approach to effecting retardance is by total internal reflection. FIGS. 3a and 3b show retardance vs. internal angle and wavelength, (at a given angle), for the fused silica/air interface. Note that the change in retardance vs. wavelength for total internal reflectance is very small compared to the (1/wavelength) dependence of birefringence-induced retardance. Fresnel rhomb retarders which are based on this effect are readily available. However, a typical ¼ wave Fresnel rhomb design translates the beam significantly, and the retardance also changes significantly as a function of beam angle, making it impractical to use a Fresnel rhomb in a rotating compensator style ellipsometer or polariineter design. FIG. 4a shows a Typical Wave ¼ wave 90 degree retardance Fresnel Rhonib and demonstrates the translation effect. FIG. 4b shows a known approach to combining two Fresnel Rhombs to achieve a substantially non-translated beam. The rhombs each have first (RS1), second (RS2), third (RS3) and forth (RS4) sides, said first (RS1) and third (RS3) sides being parallel to one another, and said second (RS2) and forth (RS4) sides being parallel to one another, said first (RS1) and second (RS2), and said third (RS3) and forth (RS4) sides meeting one another at angles greater than ninety degrees therebetween, and said second (RS2) and third (RS3) sides and said first (RS1) and forth (RS4) sides meeting one another at angles less than ninety degrees therebetween. Note that said at least two parallelogram shaped rhombs are oriented with their first (RS1) and third (RS3) sides being substantially parallel to one another. In use a beam of electromagnetic radiation caused to enter the first (RS1) side of one thereof, at a substantially normal angle thereto, then proceeds so that it internally reflects from said second (RS2) and forth (RS4) side thereof, then exits said third (RS3) side thereof in a direction such that it then enters the first (RS1) side of another thereof at a substantially normal angle thereto, then proceeds so that it internally reflects from said second (RS2) and forth (RS4) side thereof, then exits said third (RS3) side thereof. Said system is distinguished over known configurations in that it is characterized in that at least one of the sides (RS1) (RS2) (RS3) (RS4) of at least one of the parallelogram shaped rhombs has a coating thereupon which has a different refractive index than does the material from which said corresponding parallelogram shaped rhomb is comprised. Preferred practice is to coat sides (RS2) and (RS4) of each rhomb. The angles of the parallelogram shaped rhomb can be 36, 144, 36, and 144 degrees or 45, 135, 45 and 135 degrees, and the rhombs can be fabricated from of fused silica, with the coating being a material, (eg. $MgF_2$), with a lower refractive index.

Figure 4C:
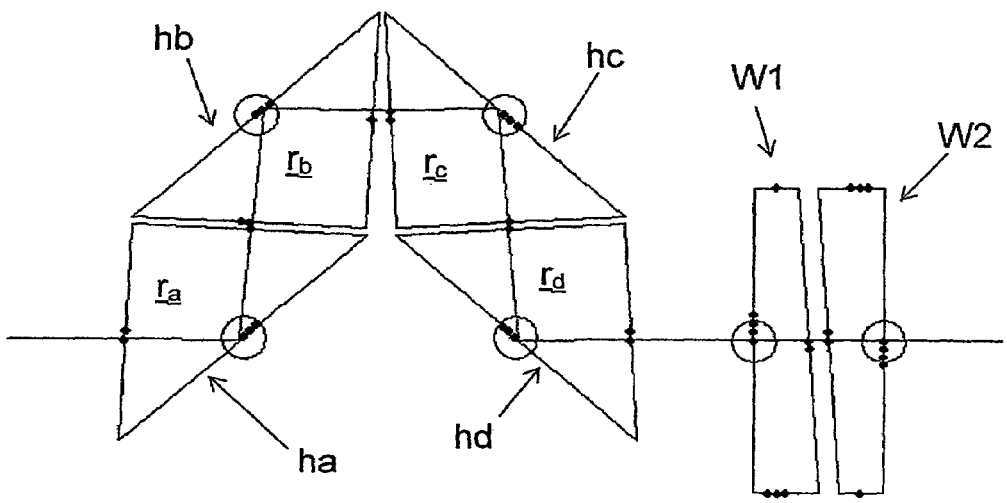
FIG. 4c shows a variation on the FIG. 4b system comprising four right angle prisms and optional wedge elements as also shown in FIG. 12b.
Figure 4A:
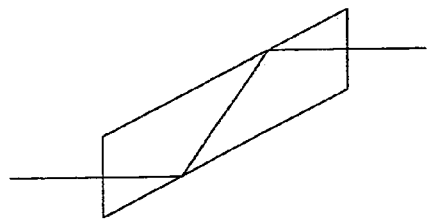
FIG. 4a shows a Typical ¼ Wave 90 degree retardance Fresnel Rhomb and demonstrates the translation effect.
Figure 4B:
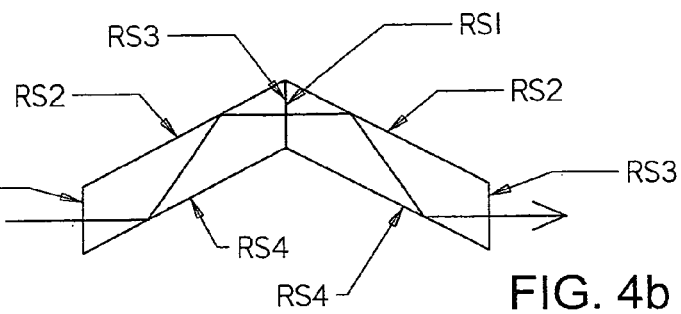
FIG. 4b shows how two Fresnel Rhombs can be combined to result in a non-deviated beam.
Figure 4D:
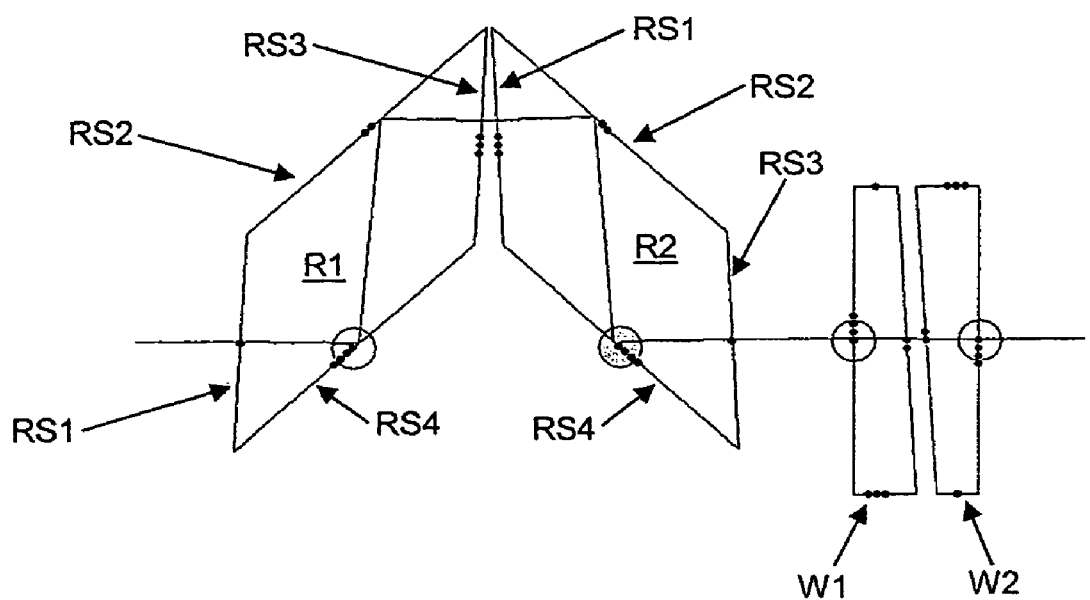
FIG. 4d shows how two Fresnel Rhombs, each of which is equivalent to two right angle prisms in FIG. 4c, and two wedges, can be combined to result in a non-deviated beam.

FIG. 4c shows a variation on FIG. 4b which is believed new and novel even without surface coatings. Shown are four similar right angle prisms, (ie. first (za), second (rb), third (rc) and forth (rd)), having sides opposite their right angles of, respectively, (ha) (hb) (hc) and (hd). As viewed in FIG. 4c the first right angle prism (ra) is positioned so that its side (ha) opposite the right angle thereof is facing downward and to the right. Directly above the first right angle prism (ra) is the second right angle prism (rb), which is oriented so that its side (hb) opposite the right angle thereof is facing upward and to the left. Directly to the right of the second right angle prism (rb) is the third right of right angle prism (rc) which is oriented so that its side (hc) opposite the right angle thereof is facing upward and to the right. Finally, positioned directly below the third right angle prism (rc) is the forth right angle prism (rd), oriented so that its side (hd) opposite the right angle thereof is facing downward and to the left. Note that the sides of each element (ra) (rb) (rc) and (rd) adjacent to the right angles thereof are identifiable as "right angle sides". It is also noted that the sides of elements Cra) (rb) (rc) and (rd) opposite the right angles can be coated with a material of different refractive index material, (eg. where said elements are made of fused silica the coating can be, for instance, 35 nm of lower index $MgF_2$). Such a coating makes the retardance entered by a total internal reflection from a side opposite the right angle thereof substantially achromatic with range of retardation. Also shown in FIG. 4c are two optional Wedge Elements (w1) and (w2), the purpose of which is described with respect to FIG. 12b. It is noted that the design of FIG. 4b is also believed to be new and novel when a coating is applied to a reflective outer surface thereof. FIG. 4d shows how two Fresnel Rhombs (R1) (R2) which are equivalent to the four right angle prisms (ra)+ (rb) and (rc)+(Rd) of FIG. 4c, and two wedges (w1) (w2), can be combined to result in a non-deviation of a beam (B) caused to pass therethrough. The angles of the Rhombs are 45, 135, 45 and 135 degrees. Coatings with a different refractive index from that of the material from which the Rhomb is comprised can be present on surfaces thereof as well, much as for the system in FIG. 4b.

It is noted that when applying the embodiments of FIGS. 4b and 4d, the Beam (B) is typically not entered exactly along a normal to the surface entered, (eg. (RS1) in FIG. 4d). This diverts unwanted reflections and such a beam entry locus can be termed "substantially normal" to the surface where the off-normal angle is sufficient to divert said reflections. Also, as presented with respect to FIG. 12b, the Wedges (w1) (w2) can be rotated with respect to one another and/or simultaneously to result in a non-deviated beam, (B).

Figure 3C:
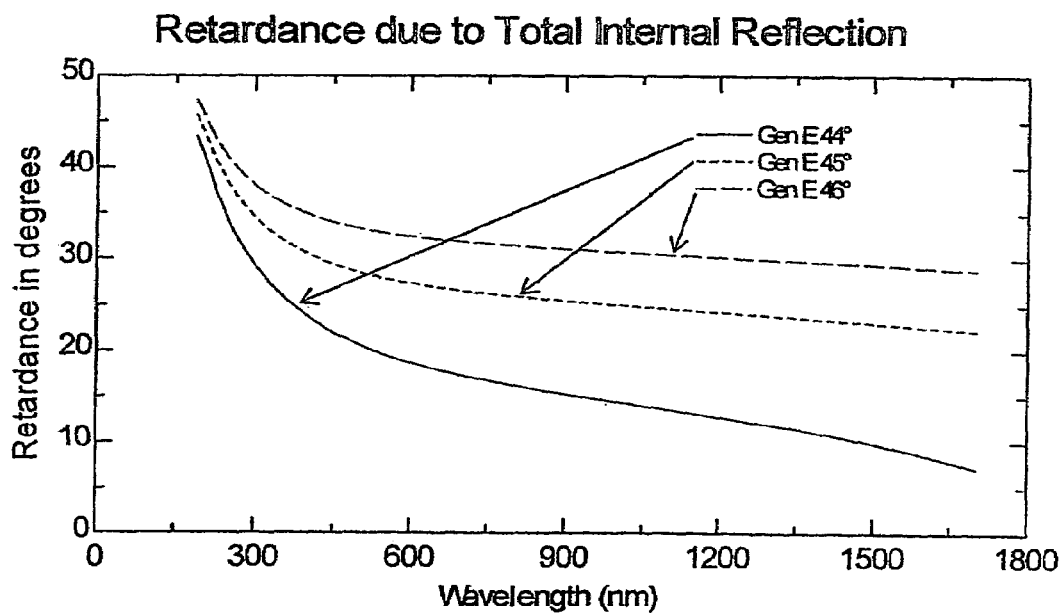
FIG. 3c shows retardance vs. and wavelength, (at a given angle), for the fused silica/air interface for a system as shown in FIG. 4c.
Figure 3A:
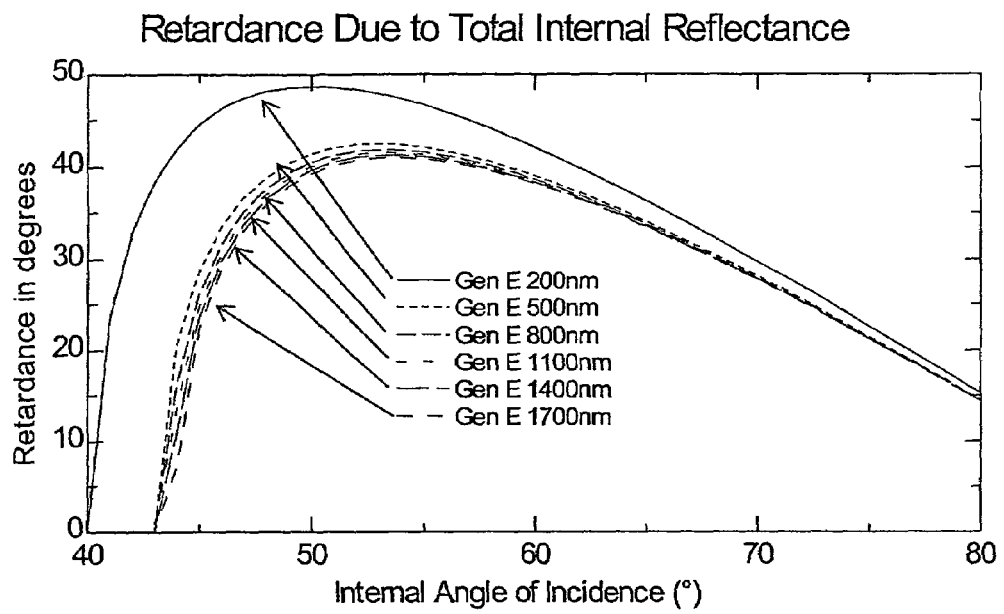
FIGS. 3a and 3b show retardance vs. internal angle and wavelength, (at a given angle), for the fused silica/air interface.
Figure 3B:
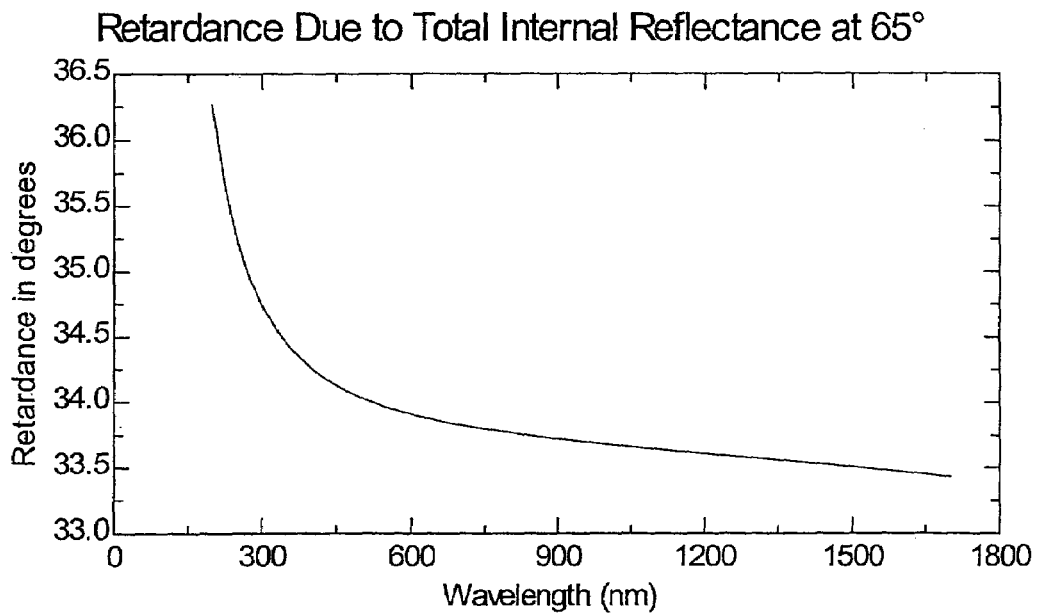
Figure 3D:
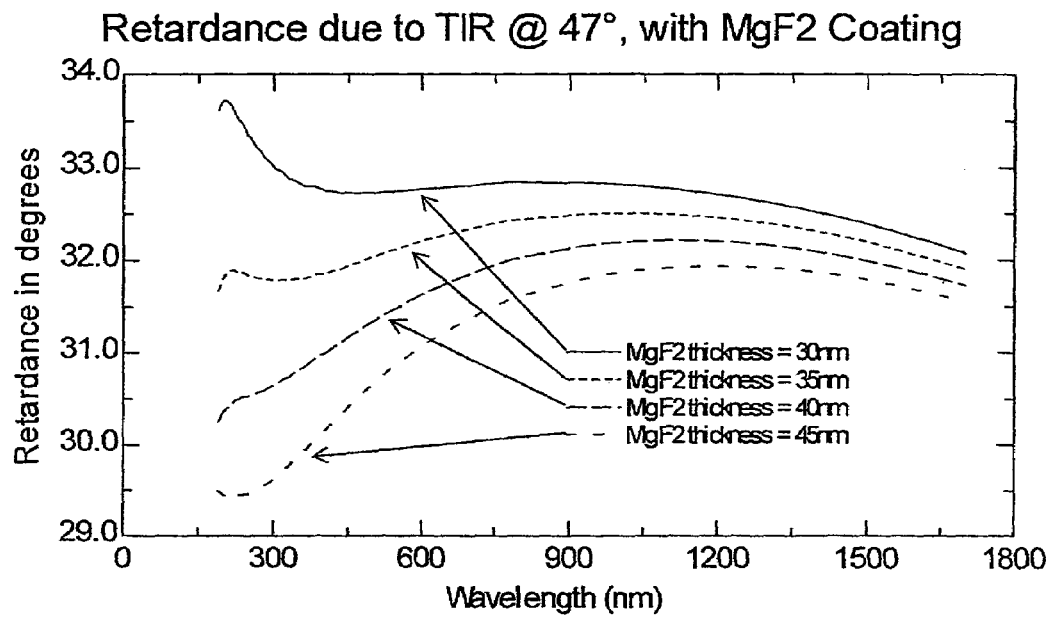
FIG. 3d show results as in FIG. 3c, but for a system having a different refractive index coating on reflective surfaces of a system as shown in FIG. 4c.

FIG. 3c shows retardance vs. internal angle and wavelength, (at a given internal reflection angle), for the fused silica/air interface for a system as shown in FIG. 4c, and FIG. 3d show results as in FIG. 3c, but for a system having a different refractive index coating on reflective surfaces of a system as shown in FIG. 4c. FIGS. 3a and 3c indicate that near a 45 degree angle of incidence the retardance varies strongly as a function of both wavelength and angle of incidence. A total retardance, resulting from four reflections, varies between 180 degrees at 190 nm to less than 90 degrees at 1700 nm. FIG. 3d indicates that including a coating on the side of the elements (ra) (rb) (rc) and (rd) opposite their right angle can make said result more achromatic. For instance, where the elements (ra) (rb) (rc) and (rd) are made from Fused Silica, and the coatings are between 30-45 nm of $MgF_2$, the total retardation for four total internal reflections in the described system is between 116 and 136 degrees over a range of wavelengths of 190 nm 1700 nm.

Figure 5:
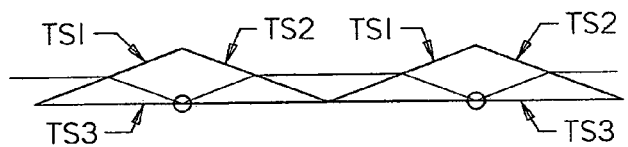
FIG. 5 shows two triangular isosceles prisms, with angles of 26, 128, and 26 degrees.

Continuing, the present invention retarder design uses an even number of multiple total internal reflections to provide the desired amount of retardance. Furthermore, the geometry of the reflections is such that a given change in the input beam angle causes opposite changes in the internal angles of reflection, and therefore. (since the slope of the retardance vs. angle curve above is relatively linear over small angle ranges), the net retardation of the system does not change to the 1st order for small changes in the beam angle. One embodiment of the new retarder system is shown in FIG. 5. Shown are two triangular isosceles prisms, each with angles of 26, 128, and 26 degrees. Each triangular shaped prisms each has:

first (TS1) and second (TS2) sides of equal length which project from one another at an angle greater than ninety degrees therebetween, and a third side (TS3) oriented opposite said greater than ninety degree angle, said at least two similar triangular shaped prisms being oriented with respect to one another such that the third (TS3) sides thereof are substantially colinear;

such that a beam of electromagnetic radiation caused to enter the first side of one thereof, at a non-normal angle thereto, is refracted so that it internally reflects from said third side thereof, then exits said second side thereof in a direction such that it then enters the first side of another thereof at a non-normal angle thereto, is refracted so that it internally reflects from said third side thereof, then exits said second side thereof. The prisms can be fabricated from of fused silica.

Figure 6:
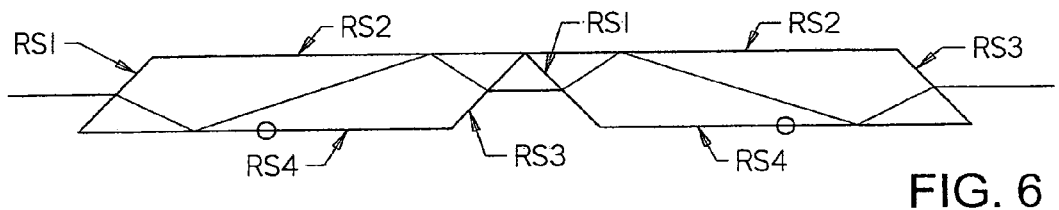
FIG. 6 shows two parallelogram rhombs, with angles of 36, 144, 36, and 144 degrees.
Figure 7A:
FIGS. 7a, 7b, 8a and 8b show that if the elements are translated up or down, the exiting beam is unchanged.
Figure 7B:
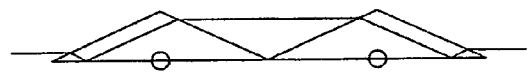
Figure 8A:
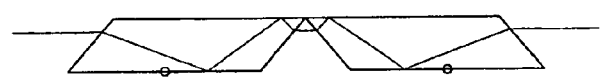
Figure 8B:
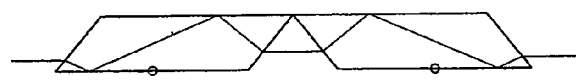

Another embodiment of the new retarder system is shown in FIG. 6. Shown are two parallelogram rhombs, with angles of 36, 144, 36, and 144 degrees. Said parallelogram shaped rhombs, each have first (RS1), second (RS2), third (RS3) and forth (RS4) sides, said first (RS1) and third (RS3) sides being parallel to one another and said second (RS2) and forth (RS4) sides being parallel to one another, said first (RS1) and second (RS2), and said third (RS3) and forth (RS4) sides meeting one another at angles greater than ninety degrees therebetween, and said second and third sides and said first and forth sides meeting one another at angles less than ninety degrees therebetween. Said at least two parallelogram shaped rhombs are oriented with their second (RS2) sides being substantially colinear and with their forth (RS4) sides thereof being substantially colinear, such that a beam of electromagnetic radiation caused to enter the first side (RS1) of one thereof, at a non-normal angle thereto, is refracted so that it internally reflects from said second (RS2) and forth (RS4) side thereof, then exits said third (RS3) side thereof in a direction such that it then enters the first (RS1) side of another thereof at a non-normal angle thereto, is refracted so that it internally reflects from said second (RS2) and forth (RS4) side thereof, then exits said third (RS3) side thereof. The parallelogram shaped rhomb can be fabricated from of fused silica.

Note that both the FIG. 5 and FIG. 6 embodiments have input and output surfaces into which a beam is entered, and out of which is exits, respectively, said surfaces serving to refract the beam in use. Other surfaces at which total internal reflection occurs are used to enter retardance. It is noted that The Fresnel losses at the refracting interfaces result in a relative attenuation for orthogonally polarized beams. The orthogonal beams are typically denoted p and s for light polarized parallel and perpendicular to the plane of incidence.

The relative attenuation and retardation of an optical element can be quantified by the equation below, which is similar to the standard ellipsometry definition. In this case, Tp and Ts are the complex amplitudes of the orthogonal beams which are transmitted through the prism, ($\psi$) is the relative attenuation, and ($\Delta$) is the retardance:

$$Tp/Ts = \tan(\psi)e^{i(\Delta)}.$$

An ideal retarder changes only the relative p-to-s phase, (ie. the retardation), of the beam, and for said case ($\psi$)=45 degrees. For the current invention, the ($\Delta$) value depends on the number and angle of refracting surfaces in the design. For the triangle design ($\psi$) is about 57 degrees, and for the rhomb design ($\psi$) is about 53 degrees. Since ($\psi$) is dependent on the index of refraction, it varies a few degrees over the 190-1700 nm spectral range). While the ($\psi$) value of the retarder does have to be determined in the ellipsometer/polarimeter system calibration, the sensitivity and accuracy of the instrument has been found to not be significantly degraded as long as ($\psi$) is not too far from 45 degrees. It is noted that the beam enters and exits the elements at near a Brewster angle of incidence, hence substantially 100% of the p polarized light is transmitted through the system.

The geometry and symmetry of the elements results in a number of very useful properties. For example, FIGS. 7a, 7b, 8a and 8b show that if the sequential elements are translated up or down as a unit, the exiting beam remains collinear with the input beam. If the sequential elements are rotated, FIGS. 9a, 9b, 10a and 10b show that the exiting beam angle is unchanged, (though it is slightly translated).

FIGS. 11a, 11b, 11c, 11d, 11e, 11f show that the most useful property of the new retarder design is that as the angle of the input beam is changed, the resulting polarization properties ($\psi$) and ($\Delta$) change very little. This is because the geometry and symmetry of the designs are such that changes in the refraction and total internal reflection angles have opposite signs for the two elements shown in the system of FIGS. 7a, 7b, 8a and 8b, which in turn cancels change in ($\psi$) and ($\Delta$) vs. input beam angle to a 1st order approximation. To give a feel for the results achieved by a present invention system, typically the change in ($\psi$) and ($\Delta$) for a one degree change in beam angle is approximately 0.01 degree. Note that FIGS. 11a-11f show that:

Beam angle=+1 degrees, ($\psi$)=56.953, ($\Delta$)=70.425;
Beam angle=0 degrees, ($\psi$)=56.940, ($\Delta$)=70.419;
Beam angle=-1 degrees, ($\psi$)=56.953, ($\Delta$)=70.425;
Beam angle=+1 degrees, ($\psi$)=52.357, ($\Delta$)=114.232;
Beam angle=0 degrees, ($\psi$)=52.349, ($\Delta$)=114.221;
Beam angle=-1 degrees, ($\psi$)=52.357, ($\Delta$)=114.232.

The net relative attenuation and retardance ($\psi$) and ($\Delta$) of the system can be controlled by adjusting the number of total internal reflections (determined by the number and length of the elements), the angles of refraction and reflection (determined by the prism and/or rhomb angles), and the material used to fabricate the elements.

Any transparent, optically isotropic material can be used for the elements, though care should be taken in mounting the elements to minimize strain-induced birefringence. Fused silica is ideal for the UV-VIS-NIR spectral range, but CaF2 is preferable in the DUV, and Si, Ge, ZnSe, KRS$_5$, etc. are suited for use in the IR. Presently, preferred embodiment designs use fused silica, and have the following properties over a wide 190-1700 nm spectral range:

triangular prisms: ($\psi$)=56.382-59.286;
($\Delta$)=67.801-81.290;
parallelogram rhombs:
($\psi$)=51.976-54.271;
($\Delta$)=109.795-135.7010.

Said examples are not to be considered limiting, however, and other designs are possible, using different materials, angles, and/or geometries. For instance, it might be beneficial to provide for substantially normal angle entry and exit thereby avoiding the effect on ($\psi$), but the key element of any design is that symmetry is employed to enable the following properties:

1. The locus of the beam is not deviated as the system is translated;
2. The angle of the beam locus is not deviated as the system is rotated;
3. The change in polarization properties are minimal for changes in the input beam angle.

Another beneficial aspect of the disclosed design is that, since at least two elements are present, if the elements are not perfectly fabricated and/or aligned, the height and/or tilt of at least one of the elements can be adjusted with respect to the other such that the input beam is substantially undeviated in position and angle by the system. FIG. 12a demonstrates a system for accomplishing this by allowing translation and/or rotation of an element, and FIG. 12b shows an additional sequential two wedge (w1) (w2) system wherein relative rotation of one wedge with respect to the other provides a similar benefit. A system can then include at least one selection from the group consisting of:

at least one of the sequential elements has a mechanism for translating and/or tilting the element, for the purposes of aligning the system such that the output beam is substantially undeviated from said input beam;

there is present an additional sequential two wedge system wherein relative rotation of one wedge with respect to the other and/or combined wedge rotation can be performed for the purposes of aligning the system such that the output beam is substantially undeviated from said input beam.

It is also noted that when practicing Beam (B) deviation correction via Wedge (w1) (w2) rotations, relative rotation of one wedge with respect to the other and combined rotations of both Wedges (w1) and (w2) can be practiced.

It is noted that while not shown or preferred, a system could comprise such as one Triangular shaped element and one Trapezoidal shaped element. Such an arrangement can be viewed as a sequence of a FIG. 9a and FIG. 10a embodiment, perhaps with one of the FIG. 9a prisms removed and with one of the FIG. 10a rhombs removed. Careful attention to preserving effective symmetry is required in any such embodiment, however.

It is also noted that only a single primary beam is transmitted through the disclosed systems, as the secondary reflections from the refracting interfaces do not re-enter the primary beam path. This means that only a single polarization state is present in the transmitted beam. In contrast, multiple reflections from the parallel surfaces of birefringent plate retarders result in beam depolarization which can degrade the ellipsometer/polarimeter accuracy if not accounted for properly.

Figure 13:
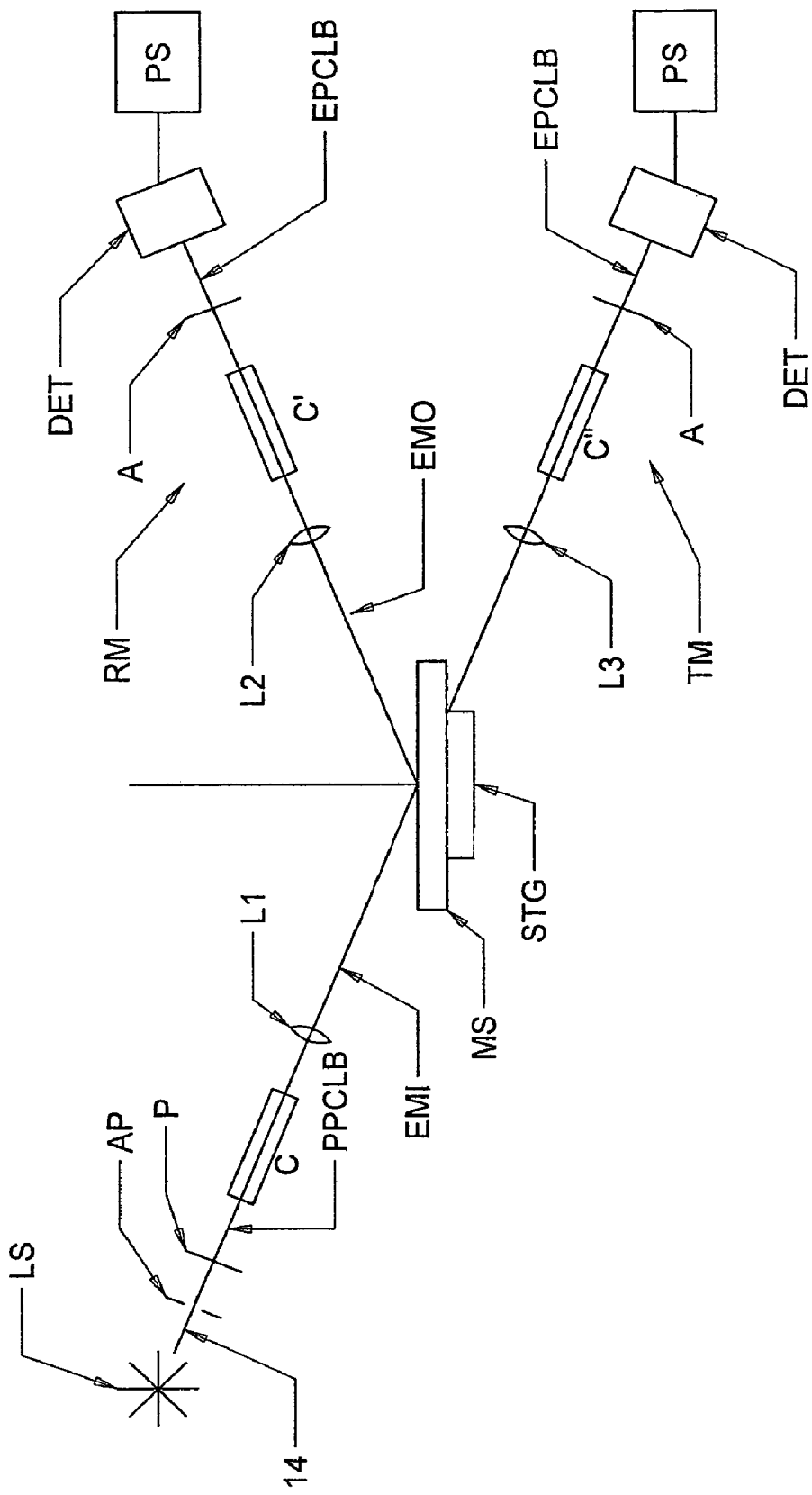
FIG. 13 shows a basic ellipsometer or polarimeter comprising at least one rotatable compensator system.

As a primary use of the sequential element system is in ellipsometer and polarimeter systems, FIG. 13 is included to show an ellipsometer or polarimeter system which, for each of a Reflection and Transmission mode, comprises:

a) a source (LS) of electromagnetic radiation;
b) a polarizer (P);
c) a stage (STG) for supporting a sample (MS);

d) an analyzer (A); and
e) a detector (DET);

said ellipsometer or polarimeter system further comprises at least one rotatable compensator (C) (C') (C") present at least one location selected from the group consisting of:
  between said source (LS) of electromagnetic radiation and said stage (STG) for supporting a sample (MS); and
  between said stage (STG) for supporting a sample (MS) and said detector (DET);

said at least one rotatable compensator (C) (C') (C") comprising at least two sequential elements oriented with respect to one another such that said entered electromagnetic beam undergoes total internal reflection at least once in each of the elements, with the orientation, geometry, and symmetry of the elements being such that the output beam position is undeviated by a translation of the system, and the output beam angle is undeviated by a rotation of the system. Again, one embodiment provides that two triangular shaped prisms are used for the elements. Preferred design provides that the angles of the triangular prisms are 26, 128, and 26 degrees, and fabrication of the prisms can be from fused silica. Another embodiment provides that two parallelogram shaped rhombs are used for the elements. Preferred design provides that angles of the parallelogram shaped rhombs are 36, 144, 36, and 144 degrees, and again, fabrication of the parallelogram can be from fused silica. Also, as mentioned other embodiments can include one or more triangular shaped prisms and one or more parallelogram shape rhombs etc. Further, at least one of the elements can have a mechanism for translating and/or tilting at least one of the elements, for the purposes of aligning the system such that the locus of the exiting beam is substantially undeviated in position and angle from the locus of the input beam.

Finally, it is noted that the coating of, for instance, a material of different refractive index material, (eg. where said elements are made of fused silica the coating can be, for instance, 35 nm of $MgF_2$, which has a lower index), applied to a totally internally reflecting surface described with respect to FIGS. 4b and 4c can be applied in any of the embodiments in FIGS. 5, 6 7a, 7b, 8a, 8b, 9a, 9b, 10a, 10b, 11a-11f and 12a and 12b. Further, such a coating can be beneficially placed on non-totally internally reflecting surfaces thereof to reduce reflections therefrom Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for introducing a relative phase retardation into orthogonally polarized components of an electromagnetic beam entered thereinto, said system consisting of at least two sequential elements oriented with respect to one another such that said entered electromagnetic beam undergoes total internal reflection at least once in each of the at least two elements;
  the sequence, orientation, geometry, and symmetry of the elements being such that the output beam position is substantially undeviated by a translation of the system, and the output beam angle is substantially undeviated by a rotation of the system.

2. A system as in claim 1 which comprises at least four sequential elements, said beam undergoing total internal reflection once in each of the elements, said system being characterized in that each of said at least four elements are right angle prisms having right angle sides adjacent to the right angle thereof and a side opposite the right angle thereof; said right angle prisms being oriented with respect to one another such that, as viewed in side elevation, the first right angle prism is positioned so that its side opposite the right angle thereof is facing downward and to the right, and so that directly above the first right angle prism is present the second right angle prism, which is oriented so that its side opposite the right angle thereof is facing upward and to the left, and so that directly to the right of the second right angle prism is the third right angle prism, which is oriented so that its side opposite the right angle thereof is facing upward and to the right, and so that directly below the third right angle prism is positioned the forth right angle prism, oriented so that its side opposite the right angle thereof is facing downward and to the left.

3. A system as in claim 2, in which the angles of the right angle prisms are 45, 90 and 45 degrees.

4. A system as in claim 2, in which the right angle prisms are fabricated from of fused silica.

5. A system as in claim 1 which is further characterized by at least one selection made from the group consisting of:
  at least one of the sequential elements has a mechanism for translating and/or tilting the element, for the purpose of aligning the system such that the output beam is substantially undeviated from said input beam;
  at least one of the sequential elements has a coating upon a surface thereof at which Internal reflection of a beam of electromagnetic radiation occurs, said coating having a different refractive index than does the material from which said corresponding element is comprised;
  at least one of the sequential elements has a coating upon a surface thereof through which a beam of electromagnetic radiation enters or exist, said coating having a different refractive index than does the material from which said corresponding element is comprised;
  there is present an additional sequential multiple wedge system in said system for introducing a relative phase retardation into orthogonally polarized components of an electromagnetic beam, wherein one said wedge can be rotated with respect to another thereof and/or both wedge can be rotated simultaneously, for the purpose of aligning the system such that the output beam is substantially undeviated from said input beam.

6. A system as in claim 2 which is further characterized by at least one selection made from the group consisting of:
  at least one of the sequential elements has a mechanism for translating and/or tilting the element, for the purpose of aligning the system such that the output beam is substantially undeviated from said input beam;
  at least one of the sequential elements has a coating upon a surface thereof at which internal reflection of a beam of electromagnetic radiation occurs, said coating having a different refractive index than does the material from which said corresponding element is comprised;
  at least one of the sequential elements has a coating upon a surface thereof through which a beam of electromagnetic radiation enters or exist, said coating having a different refractive index than does the material from which said corresponding element is comprised;
  there is present an additional sequential multiple wedge system in said system for introducing a relative phase retardation into orthogonally polarized components of an electromagnetic beam, wherein one said wedge can be rotated with respect to another thereof and/or both wedge can be rotated simultaneously, for the purpose of aligning the system such that the output beam is substantially undeviated from said input beam.

7. A system as in claim 3 which is further characterized by at least one selection made from the group consisting of:

at least one of the sequential elements has a mechanism for translating and/or tilting the element, for the purpose of aligning the system such that the output beam is substantially undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge can be rotated with respect to another thereof and/or both wedge can be rotated simultaneously, for the purpose of aligning the system such that the output beam is substantially undeviated from said input beam.

8. A system as in claim 4 which is further characterized by at least one selection made from the group consisting of:

at least one of the sequential elements has a mechanism for translating and/or tilting the element, for the purpose of aligning the system such that the output beam is substantially undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge can be rotated with respect to another thereof and/or both wedge can be rotated simultaneously, for the purpose of aligning the system such that the output beam is substantially undeviated from said input beam.

9. A method of providing a compensator system comprising at least two sequential elements oriented with respect to one another such that an entered electromagnetic beam undergoes total internal reflection at least once in each of the elements, with the sequence, orientation, geometry, and symmetry of the elements being such that the locus of output beam from said system is substantially undeviated from that of the input beam by a translation of the system, and the locus of the output beam angle is substantially undeviated from that of the input beam by a rotation of the system;

said method comprising the steps of:

a) providing a system comprising at least two sequential elements oriented with respect to one another such that entered electromagnetic beam undergoes total internal reflection at least once in each of the elements, at least one of said elements being mounted to allow translation and/or rotation thereof with respect to another of said elements;

b) causing a beam of electromagnetic radiation to enter and exit from said sequence of elements;

c) effecting translation and/or rotation of said element which is mounted to allow translation and/or rotation thereof with respect to another of said elements such that translation and/or rotation of said system causes reduced deviation of the locus of said exiting beam as compared to that of said input beam.

10. A method as in claim 9 in which the step of providing a compensator system comprising at least two sequential elements involves providing at least one element which has a coating on at least one surface thereof which has a different refractive index from that of the material from which said comprises said element.

11. A method as in claim 9 in which the step of providing a compensator system involves providing at least four sequential elements, said beam undergoing total internal reflection once in each of the elements, said system being characterized in that each of said at least four elements are right angle prisms having right angle sides adjacent to the right angle thereof and a side opposite the right angle thereof; said right angle prisms being oriented with respect to one another such that, as viewed in side elevation, the first right angle prism is positioned so that its side opposite the right angle thereof is facing downward and to the right, and so that directly above the first right angle prism is present the second right angle prism, which is oriented so that its side opposite the right angle thereof is facing upward and to the left, and so that directly to the right of the second right angle prism is the third right angle prism, which is oriented so that its side opposite the right angle thereof is facing upward and to the right, and so that directly below the third right angle prism is positioned the forth right angle prism, oriented so that its side opposite the right angle thereof is facing downward and to the left.

12. A method as in claim 11 in which the step of providing a compensator system involves providing at least four sequential elements in which the angles of the right angle prisms are 45, 90 and 45 degrees.

13. A method as in claim 11 in which the step of providing a compensator system involves providing in which the right angle prisms are fabricated from of fused silica.

14. A system as in claim 2 in which said first and second right angle prisms are merged into a single element where they contact one another, and said third and forth right angle prisms are merged into a single element where they contact one another, to form first and second sequentially oriented rhombs.

15. An ellipsometer or polarimeter system comprising:
a) a source of electromagnetic radiation;
b) a polarizer;
c) a stage for supporting a sample;
d) an analyzer; and
e) a detector;

said ellipsometer or polarimeter system further comprising at least one rotatable compensator system present at at least one location selected from the group consisting of:

between said source of electromagnetic radiation and said stage for supporting a sample; and between said stage for supporting a sample and said detector;

said at least one rotatable compensator comprising at least two sequential elements oriented with respect to one another such that said entered electromagnetic beam undergoes total internal reflection at least once in each of the elements, with the sequence, orientation, geometry, and symmetry of the elements being such that the locus of the output beam is substantially undeviated from that of the input beam by a translation of the system, and the locus of the output beam angle is substantially undeviated from that of the input beam by a rotation of the system.

16. An ellipsometer system as in claim 15 which comprises at least four sequential elements, said beam undergoing total internal reflection once in each of the elements, said system being characterized in that each of said at least four elements are right angle prisms having right angle sides adjacent to the right angle thereof and a side opposite the right angle thereof; said right angle prisms being oriented with respect to one another such that, as viewed in side elevation, the first right angle prism is positioned so that its side opposite the right angle thereof is facing downward and to the right, and so that directly above the first right angle prism is present the second right angle prism, which is oriented so that its side opposite the right angle thereof is facing upward and to the left, and so that directly to the right of the second right angle prism is the third right angle prism, which is oriented so that its side opposite the right angle thereof is facing upward and to the right, and so that directly below the third right angle prism is positioned the forth right angle prism, oriented so that its side opposite the right angle thereof is facing downward and to the left.

17. A system as in claim 16, in which the angles of the right angle prisms are 45, 90 and 45 degrees.

18. A system as in claim 16, in which the right angle prisms are fabricated from of fused silica and there is optionally present a coating of $MgF_2$ on at least one surface of at least one prism.

* * * * *